United States Patent
Koehler

[11] 3,937,099
[45] Feb. 10, 1976

[54] DEVICE FOR THE FINE ADJUSTMENT OF AN INSTRUMENT TABLE SUPPORTING AN OPTICAL EQUIPMENT

[75] Inventor: Kurt Koehler, Koenigsbronn, Germany

[73] Assignee: Carl Zeiss-Stiftung, Oberkochen, Germany

[22] Filed: Feb. 7, 1975

[21] Appl. No.: 547,807

[30] Foreign Application Priority Data
Mar. 19, 1975 Germany............................ 2407174

[52] U.S. Cl............................................ 74/471 XY
[51] Int. Cl.² ......................................... G05G 9/00
[58] Field of Search ........... 74/471 R, 471 XY, 473; 33/174 TA

[56] References Cited
UNITED STATES PATENTS

| | | | |
|---|---|---|---|
| 1,923,290 | 8/1933 | Wood | 74/471 |
| 2,610,520 | 9/1952 | Snow | 74/471 |
| 3,091,130 | 5/1963 | Payerle et al. | 74/471 |
| 3,625,302 | 12/1971 | Lauck | 74/471 |

*Primary Examiner*—Benjamin W. Wyche
*Assistant Examiner*—Weeley S. Ratliff, Jr.
*Attorney, Agent, or Firm*—Nichol M. Sandoe

[57] ABSTRACT

A device for the fine adjustment of an instrument table supporting an optical instrument which is operated by a control lever which is pivotally mounted to swivel in any direction to effect adjustment of the table in the horizontal plane and which is rotatable to effect vertical adjustment of the table.

4 Claims, 3 Drawing Figures

DEVICE FOR THE FINE ADJUSTMENT OF AN INSTRUMENT TABLE SUPPORTING AN OPTICAL EQUIPMENT

This invention relates to a device for the fine adjustment of an instrument table supporting an optical instrument, as for example, an opthalmological instrument, which said device is operated by a control lever which is pivotally mounted to swivel in any direction to effect adjustment of the table in the horizontal plane and which is rotatable to effect vertical adjustment of the table.

Tables for opthalmological instruments are known in the prior art which, for the purposes of making coarse adjustments, can be moved in the horizontal plane in two directions at right angles to each other by means of appropriately arranged guides. Fine adjustments in the horizontal plane are effected by means of a control lever which is arranged at right angles to the plane of the instrument table and is mounted on a ball joint to swivel in any direction. By means of this lever, the instrument can, for example, be adjusted first to one of the patient's eyes and then to the other.

It is desirable to be able to effect also a vertical adjustment of the instrument without having to move the hand from one control member to another.

To achieve this, it is known in the prior art to encircle the control lever which serves for fine adjustment in the horizontal plane with a rotating ring which, via a gear belt is connected to a gearwheel which in turn raises or lowers the instrument table by means of a vertical adjustment spindle. With such a design, it is difficult to effect fine adjustment in the horizontal plane at the same time effect delicate vertical movement since the operator cannot actuate the rotatable ring and the control lever at the same time with one hand.

It is also known in the prior art to provide the fine adjustment control lever with a rotary knob which, via a spindle inside the lever, acts upon a universal joint, which via a shaft and gear moves a verticle spindle. The fine adjustment control lever is connected at its lower end with a ball in the center of which the universal joint is arranged, the ball itself riding on the base plate of the instrument table. Apart from the fact that horizontal movement is very restricted, delicate vertical adjustment is difficult since the rotary knob cannot be actuated by the entire hand but by the fingers only.

Finally, a device is also known in the prior art in which the fine adjustment control lever is rotatable as a whole about its own axis and thus effects a vertical adjustment. The control lever is mounted in a sleeve and can swivel freely in any direction. As far as rotation is concerned, however, the lever is operatively connected with said sleeve and rotates therewith. This connection is effected either by means of friction or by a known universal joint. Thus, the sleeve is driven by rotation of the lever and actuates a vertical spindle via a gear wheel.

Since with this design the sleeve serves simultaneously as a pivot bearing and as a bearing for the swivelling movement of the control lever, radial forces are produced in the pivot bearing. These have an adverse effect on the bearing and result in the operator having to apply differing degrees of force when rotating the lever in its neutral position and during a swivelling movement thereof.

It is the object of the present invention to provide a device for the fine adjustment of an instrument table supporting an optical instrument, as for example, an opthalmological instrument, which enables the operator to make a uniformly smooth adjustment in both the horizontal and vertical planes by means of a single control lever which can be actuated to make either or both adjustments without changing the position of the operator's hand.

According to the present invention, the device is operated by a control lever which is pivotally mounted to swivel in any direction to effect adjustment in the horizontal plane, and which is also rotatable to effect vertical adjustment. The lever comprises a hollow sleeve which serves as a handle, and the bottom end of the sleeve is connected via a universal joint to a rotatable gear-wheel which, in turn, via further gear systems, serves to raise and lower the instrument table. A rod extends into said hollow sleeve and during the swiveling action of the lever around the pivot defined by the universal joint, said rod swivels with said sleeve without any lost motion, but it does not rotate with said sleeve. The lower end of said rod engages a part of the instrument table which rests upon a horizontal base. The rod is provided with a spherical bulge which is located below the plane of said universal joint and which is so supported as to produce horizontal displacement of the entire instrument table whenever said control lever is swivelled.

Thus, the device comprises a single operating control lever for the control of both horizontal and vertical displacements which can be grasped by the operator with his entire hand. This operating control lever functionally operates two sets of parts, each serving a different purpose and each having its own bearings. This ensures that no radial forces are exerted upon the pivot bearing, and that consequently exactly the same amount of force is required to rotate the handle irrespective of its swivelled position.

It is particularly important to arrange the spherical bulge of the inner rod between its lower end and the pivot point defined by the universal joint. Thereby, the bearing that governs the horizontal displacement of the instrument table is positioned below the pivot about which the control lever is swivelled so that the swivel motion transmitted to the instrument table is reduced. Thus, any unintentional swivel occurring when the hollow sleeve is rotated in order to effect a vertical displacement, is prevented from acting direct upon the horizontal setting. The designer has the opportunity to choose freely the degree of reduction by choosing the distance between the pivot point of the stick and the spherical bulge.

A preferred embodiment of the invention is shown in the accompanying drawings, in which.

Figure 1:
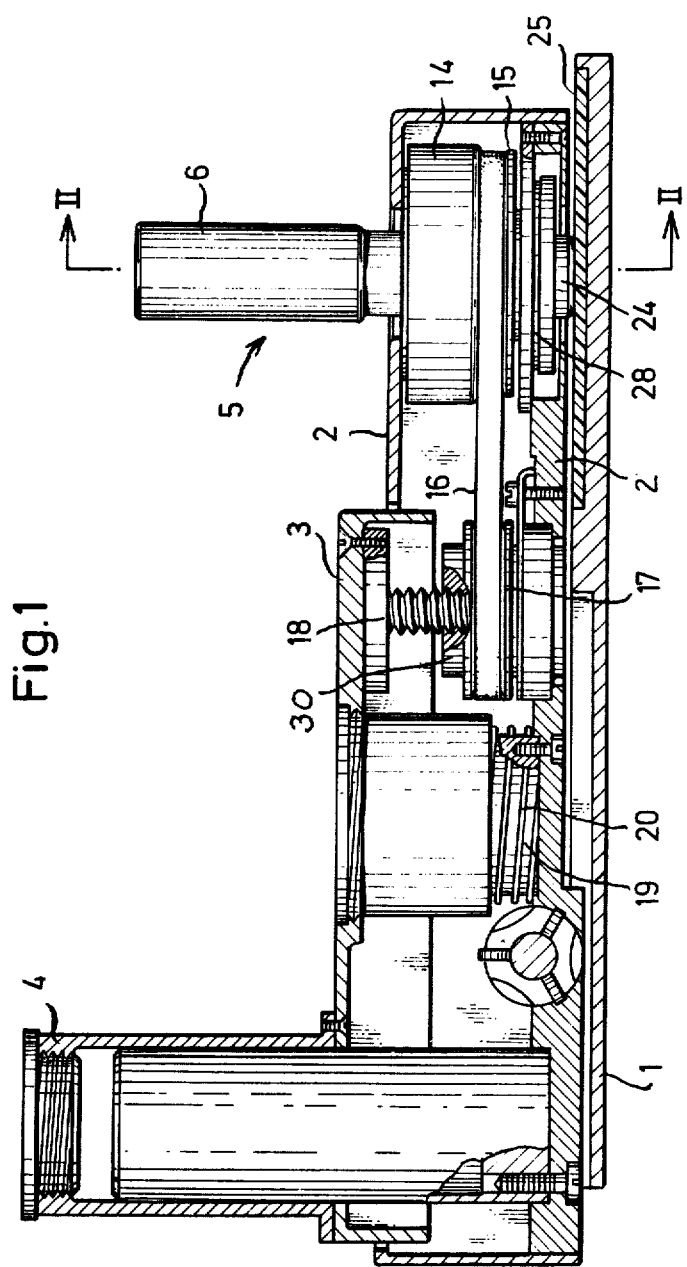
FIG. 1 is a front view of the device in which the housing is cut away.

Reference numeral 1 designates a horizontal base plate supporting an instrument table 2 which can be manually moved for coarse adjustment in both longitudinal and transverse directions in a conventional manner and by means of appropriately arranged guides not shown here.

The instrument table 2 carries the instrument support proper, which comprises an instrument support plate 3 and a tube 4 and is vertically adjustable with respect to the table 2. An optical instrument, such as an opthalmological instrument may be mounted on the tube 4.

The fine adjustment of instrument table 2 in the horizontal plane and the vertical adjustment of the instrument support plate 3 with respect thereto are both effected by a control lever 5 consisting of a hollow sleeve 6 and an inner rod 7.

The sleeve 6 is pivotally connected with a ring 10 by means of two bolts 8 and 9, and said ring is pivotally connected with a gearwheel 13 by means of bolts 11 and 12 to form a universal joint which defines the pivot point about which the control lever 5 can be swivelled.

As can readily be seen, in each position of the control lever 5, the sleeve 6 can be rotated about its vertical axis, thereby rotating gearwheel 13 via the universal joint 8–12. Said gearwheel carries a gear belt 16 which is held between rings 14 and 15. Rotation of the sleeve 6 produces rotation of the gearwheel 13 which is transmitted via the gear belt 16 to gearwheel 17, which is combined with a tubular sleeve 30. This sleeve is equipped with an inside thread within which a vertical threaded spindle 18 is mounted, so that rotation of gearwheel 17 causes vertical movement of said spindle. The spindle 18 presses against the instrument support plate 3 so that vertical movement of the spindle displaces this support plate together with tube 4 in vertical direction.

Between the vertical spindle 18 and the tube 4 there is arranged a cylindrical shell 19 which is surrounded by a helical spring 20 which is under compression. This spring presses against the bottom of the instrument table 2 and against the support plate 3 and provides a counter-force for the vertical adjustment of instrument support 3 and tube 4.

In the embodiment illustrated, the inner rod 7 has three spherical bulges 21, 22 and 23. The rod 7 is so mounted within sleeve 6 by means of the upper sphere 21 that when the control lever 5 is swivelled around the pivot defined by the universal joint, rod 7 swivels with sleeve 6 without any lost motion, but it does not rotate with said sleeve because the frictional forces between the bulges 22 and 23 and the members 26 and 24, respectively, are greater than the frictional force between the bulge 21 and the sleeve 6.

The lower spherical end 23 of rod 7 engages a cup located in an intermediate plate 24 which rests upon a pad 25 of synthetic material connected to plate 1.

The spherical bulge 22 is mounted in an aperture in a ring 26, relative to which the gearwheel 13 can be rotated by means of a ball bearing 27.

When the control lever 5 is swivelled, the inner rod 7 swivels about the pivot defined by the universal joint, thereby shifting the instrument table 2 in horizontal direction by way of the linkage 22, 26. The table then slides over intermediate plate 24 which is fitted with a self-lubricating ring 28. The plate 24 is held stationary by friction between pad 25 and the bottom surface of plate 24.

Figure 2:
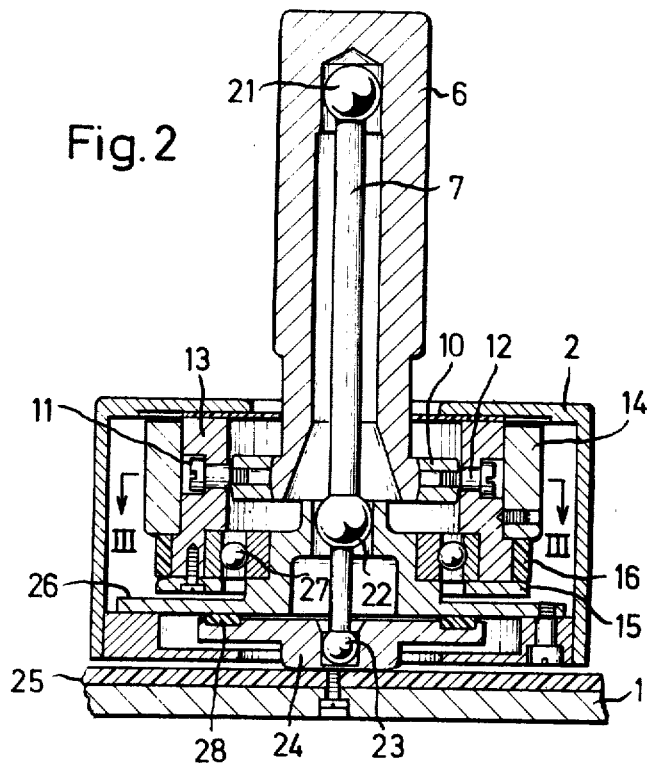
FIG. 2 is a section on the line II—II of FIG. 1.
Figure 3:
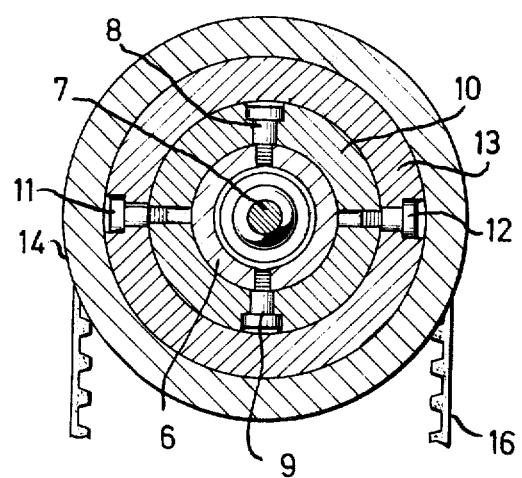
FIG. 3 is a section on line III—III of FIG. 2.

As is evident from FIGS. 1–3, the control lever 5 of the device is carried in two separate bearings, one of which defined by the universal joint 8–12, transmits only the rotation of the sleeve 6 necessary for vertical adjustment of the instrument support 3, 4. The other bearing 22, 26 supports the inner rod 7, causing the instrument table 2 to be displaced horizontally whenever the control lever 5 is swivelled. This horizontal displacement is accomplished with a certain reduction. The extent of this reduction is defined by the relationship of the distance between the pivot of the universal joint and the lever end 23 to the distance between points 22 and 23.

What is claimed is:

1. A device for the fine adjustment of an optical instrument, comprising a base plate, an instrument table including an instrument support plate for supporting said optical instrument, an intermediate plate resting upon said base plate, a control lever, said control lever comprising a hollow sleeve and a rod extending into said sleeve and engaging said sleeve without lost motion, said sleeve being rotatable about its longitudinal axis, a universal joint mounted on the lower end of said sleeve on which said control lever swivels in all directions about a pivot point defined by said universal joint, a gearwheel mounted on said universal joint and rotatable with said sleeve and universal joint, and means connected with said gearwheel and operable on rotation of said sleeve to raise and lower said instrument support plate, said rod being pivotally connected to said intermediate plate at its lower end and being pivotally connected to said instrument table at a point below said pivot point of said universal joint to produce horizontal displacement of said instrument table when said control lever is swivelled.

2. A device as claimed in claim 1 in which said pivotal connection between said rod and said instrument table comprises a spherical bulge on said rod located between the lower end of the rod and the pivot point defined by said universal joint.

3. A device as claimed in claim 1 in which said means connected with said gearwheel includes a vertical threaded spindle, a gearwheel mounted thereon, and a gear belt connecting said gearwheels.

4. A device as claimed in claim 3 including a cylindrical shell mounted on said instrument table between said spindle and said optical instrument, and a compression spring surrounding said shell which presses against the instrument table and against said instrument support plate.

* * * * *